(12) United States Patent
Van Wesenbeeck et al.

(10) Patent No.: US 6,446,487 B1
(45) Date of Patent: Sep. 10, 2002

(54) METHOD FOR MEASURING THE QUANTITY OF HEAT PRESENT IN FUEL GAS

(75) Inventors: Petrus J. M. M. Van Wesenbeeck, Groningen (NL); Manfred Jaeschke, Dorsten (DE); Johannes A. Schouten, Monnickendam (NL)

(73) Assignees: N.V. Nederlandse Gasunie, Groningen (NL); Ruhrgas Aktiengesellschaft, Essen (DE)

( * ) Notice: Subject to any disclaimer, the term of this patent is extended or adjusted under 35 U.S.C. 154(b) by 0 days.

(21) Appl. No.: 09/585,572

(22) Filed: Jun. 2, 2000

(30) Foreign Application Priority Data

Jun. 4, 1999 (EP) .............................................. 99201766
Jul. 29, 1999 (EP) .......................................... 99202501

(51) Int. Cl.$^7$ .............................................. G01N 19/10
(52) U.S. Cl. ...................................................... 73/23.2
(58) Field of Search ................................. 73/23.1, 23.2, 73/23.28, 30.01; 374/36, 37; 702/30; 436/143, 147

(56) References Cited

U.S. PATENT DOCUMENTS 6,244,097 B1 * 6/2001 Schley et al. ................. 73/23.2

FOREIGN PATENT DOCUMENTS

DE          19736528     * 2/1999 .......... G01N/33/22

* cited by examiner

Primary Examiner—Hezron Williams
Assistant Examiner—Jay L. Politzer
(74) Attorney, Agent, or Firm—Pillsbury Winthrop LLP (57) ABSTRACT

Method for measuring and/or regulating a quantity of heat contained in a fuel gas, the calorific value of the fuel gas being used as an input parameter, in which method a) the fuel gas or a part-stream of the fuel gas is guided through a volumetric meter or a mass flow meter, and the volumetric flow rate or the mass flow rate is measured, b) the speed of sound of the gas is determined under first reference conditions, c) one of the measurement variables dielectric constant, speed of sound under second reference conditions, carbon dioxide content of the fuel gas, nitrogen content of the fuel gas or density under standardized conditions is recorded; and d) the quantity of heat supplied is derived from these parameters, together with the calorific value of the fuel gas, as a measurement variable or control variable.

6 Claims, 8 Drawing Sheets

METHOD FOR MEASURING THE QUANTITY OF HEAT PRESENT IN FUEL GAS

The invention relates to a method for measuring and/or regulating the quantity of heat which is present in a fuel gas and is supplied to a gas-consuming device, in particular a natural-gas-consuming device, the calorific value of the fuel gas being used as an input variable.

In known measurement methods of this nature, the amount of gas supplied and the heat properties of the fuel gas are often determined. The conditions, in particular the temperature and pressure, under which these values are determined generally differ for each measurement variable.

For example, the amount of gas supplied is often measured under operating conditions, while the heat properties are often determined under standardised conditions, such as for example the normal conditions 0° C. and 1.01325 bar(a). To determine the quantity of heat, it is important for uniform temperature and pressure conditions to be observed both for the amount of gas supplied and the thermal properties. In practice, the amount of gas supplied is to this end generally converted to standardised conditions, for example the normal conditions 0° C. and 1.01325 bar(a). This conversion is known as 'volume conversion'.

The quantity of heat supplied to the gas-consuming devices can be determined by means of direct and indirect methods. In indirect methods, the composition of a natural gas is determined by means of gas chromatography, for example. Then, on the basis of this gas composition, the parameters for the volume conversion are calculated and the calorific value of the fuel gas is determined using the calorific values of the pure substances. Although these methods provide very accurate results, they have the drawback of being technically complex and therefore expensive. As a result, it is impossible to use these methods in private households, for example. In contrast to indirect methods, in direct methods the calorific value is determined directly. Commercially available calorific-value meters indicate the calorific value, generally under standardised conditions, such as for example normal conditions (0° C. and 1.01325 bar(a)). Usually, the volume conversion which is required to determine the flow of energy is derived from density measurements under standardised conditions, such as for example normal conditions (0° C. and 1.01325 bar(a)), and the conditions of the volumetric flow measurement. However, volume conversion based on density measurements are technically complex. Moreover, density cells of this nature have to be calibrated at regular intervals.

The object of the invention is to reduce the effort involved in the direct measurement and/or regulation of the quantity of heat supplied to consumption devices and, in particular, to provide a reliable and accurate measurement method.

According to the invention, this object is achieved by the fact that, in the method referred to in the introduction, the fuel gas or a part-stream of the fuel gas is guided through a volumetric meter or a mass flow meter, and the volumetric flow rate or the mass flow rate is measured, the speed of sound of the gas is determined under first reference conditions, one of the measurement variables dielectric constant, speed of sound under second reference conditions, carbon dioxide content of the fuel gas, nitrogen content of the fuel gas or density under standardised conditions, for example normal conditions (0° C. and 1.01325 bar(a))is measured; and the quantity of heat supplied is derived from these parameters, together with the calorific value of the fuel gas, as a measurement variable or control variable.

The advantage of this method lies in the fact that there is no need to carry out any density measurements under any conditions apart from standardised conditions. In most embodiments, there is no need to carry out any density measurement at all.

Particularly accurate results can be achieved for fuel gases whose calorific value at normal conditions is from 20 to 48 Mj/m3, whose relative density compared with dry air is from 0.55 to 0.9, whose proportion of carbon dioxide is less than or equal to 0.3 and whose proportion of hydrogen and carbon monoxide is less than 0.1 and 0.03 respectively. Particularly suitable measurement conditions are temperatures in the range from 225 to 350 K and pressures of less than or equal to 6 MPa.

Operating conditions are the actual conditions in the installation, for example a gas conduit, containing the gas of which the quantity of heat is measured or controlled. Reference conditions can be chosen freely within the specified ranges, preferably corresponding to conditions at which the relevant parameters are known from one or more reference gases. By standardised conditions are denoted conditions that are more generally used in the relevant technical field like normal conditions (0° C. and 1,01325 bar(a)) and standard conditions (15° C. and 1,01325 bar(a)).

The first reference conditions set are preferably normal conditions or a pressure in the range from 1 to 10 bar, more preferably from 3 to 7 bar. Although the temperature is not very critical and can be selected within a wide range, for technical reasons the temperature is above 225 K, for example from 270 K to 295 K. For the second reference conditions, a pressure of above 30 bar is preferably set. Although the temperature is not very critical and can be selected within a wide range, for technical reasons the temperature is from 225 K to 350 K.

The operating conditions are most preferable for this parameter.

The speed of sound at the reference conditions mentioned, including operating conditions, can be determined in a separate measuring unit, for example via the resonant frequency of vortex pipes or of hollow bodies or a distance travelled-time measurement, e.g. in ultrasonic flow meters.

In practice, there are various proven measurement methods available for measuring the volumetric flow rate, for example turbine flow meters or ultrasonic flow meters.

The dielectric constant can be measured inexpensively and with high accuracy even under operating conditions. The proportion of carbon dioxide is simple to determine under all conditions mentioned using known measuring instruments, e.g. by measurement of the light absorption in the infrared region.

The use of the density under normal conditions is advantageous in particular when, in the arrangement, a volume conversion is at the same time being carried out on the basis of density measurements. The use of a speed of sound measurement instead of the density measurement under operating conditions offers the advantage that the most critical component is exchanged, while there is no need to spend money on measuring other variables.

Consequently, the three measurements which are required can each be carried out reliably, accurately and without a high level of technical effort, so that linking the measured values provides suitable results for measuring and/or regulating the quantity of heat supplied to gas-consuming devices.

To establish the reference conditions, the parameters temperature and pressure are required. These can be additionally measured in step b). If a lower measurement accuracy is permissible, the values estimated from practice can also be used for these parameters.

If the calorific value does not change, or changes only slightly, such as for example in the case of a gas emanating from the same source, it is sufficient to introduce a fixed value for the calorific value into the calculation of the quantity of heat. In the event of substantial fluctuations in the calorific value of a gas flow, as may occur, for example, in collection networks, it is recommended that the calorific value be determined at regular intervals or continuously. To this end, the calorific value can be recorded inexpensively and with a high level of accuracy using various proven measurement methods, such as for example controlled catalytic oxidation of the gas to be tested.

In total, there are five variations on the method according to the invention for measuring the quantity of heat supplied of fuel gas.

In all the variants, the speed of sound is recorded under first reference conditions and the calorific value is determined or input as a constant.

In addition, in the first variant the speed of sound is also recorded under second reference conditions. Recording two speeds of sound has the advantage that the second measurement can be carried out in the same measuring device. The pressure in the apparatus can be varied by compressing the measurement volume or allowing it to expand. During the compression or expansion, the temperature of the fuel gas also changes, making it easier to set altered reference conditions. If desired, the measuring device for determining the speed of sound may also be equipped with means for varying the temperature setting. In addition, in the second variant, the dielectric constant is also measured, preferably at a pressure of at least 10 bar, e.g. under second reference conditions, e.g. operating conditions, in order to achieve a high level of accuracy.

In the third variant, the carbon dioxide content of the fuel gas is also determined.

The determination of the dielectric constant and of the carbon dioxide content may be carried out in the same measurement environment as that in which the speed of sound is determined. This allows the measuring device to be extremely compact.

In contrast to the third variant, in the fourth variant the nitrogen content is also determined, instead of the carbon dioxide content.

In the fifth variant, the density is additionally recorded under normal conditions. This variant offers advantages especially when refitting an existing volume-conversion installation which is based on density measurement, since in this specific situation it is sufficient to use only one speed of sound recording instead of the density measurement under operating conditions. As a result, on the one hand, the volume conversion is considerably simplified and is made easier to control, while, on the other hand, the existing instrumentation is used to its maximum possible effect.

Advantageously, the speed of sound is recorded under second reference conditions and the dielectric constant or the carbon dioxide content is recorded under the same reference conditions, preferably under operating conditions, in a common measurement environment. In this way, only one temperature and pressure measurement, and consequently only one thermostat, are required in order to produce or maintain the reference conditions. Moreover, uniform reference conditions for the various measurements increase the accuracy with which the quantity of heat supplied can be determined.

Recording at least one speed of sound in addition to the calorific value offers the further advantage that it is possible to dispense with determining the density of the fuel gas under operating conditions. Apparatus for measuring the density at operating conditions are expensive and complex. Preferably, in the method according to the invention, in particular if the carbon dioxide content is recorded as the third measurement variable, no additional density measurement is carried out.

To find a suitable correlation between the set of parameters applied in the method according to the invention, for example between the speed of sound under first reference conditions, the speed of sound under second reference conditions, the calorific value and the density under operating conditions and standardised conditions, it is advantageous to precede the respective steps b) and c) at least once by a plurality of measurement cycles in which step b) is carried out using a plurality of reference gases of known calorific value. The parameters required for the various variants of the method are then measured on the reference gas. In these reference cycles, a number corresponding to the number of measurement cycles of reference signal patterns determined from the ratio of the various signals measured are stored with assignment to the known densities at operating and standardised conditions. The signal pattern from a future measurement cycle on fuel gas of the unknown density at operating or standardised conditions is compared with the reference signal patterns so as to assign a particular density at operating or standard conditions.

To increase the reference accuracy, many reference cycles in which the various parameters are varied in succession over the expected measurement range should be carried out. An unambiguous and accurate assignment of a particular density at operating or standardised conditions to a signal pattern of a fuel gas determined in a measurement cycle is achieved by interpolation of the various reference signal patterns.

A significant advantage is that the correlation between densities at operating and/or standardised conditions and measured parameters only has to be found once for a specific application by means of any desired number of reference cycles. The one-off effort is comparatively low. The reference conditions should here be selected so as to correspond as closely as possible to the measurement conditions expected later. Thus, for all parameters only the measurement ranges which actually come into question should be determined with sufficient accuracy as reference signal patterns.

If the composition of the fuel gas may display greater variations, it is generally necessary to determine more reference signal patterns.

Large quantities of data are already available in relation to the dependency of the gas composition on the speed of sound and the density. Using this available data therefore makes it possible to calculate the calorific value, the speeds of sound and the density under operating conditions and standardised conditions as a function of the gas composition in the relevant area. It is thus possible to replace expensive measurements with calculations.

A preferred embodiment of the invention is characterised in that the respective proportion of a specified number of alkanes, including methane, is determined by determining the proportion of the individual alkanes, excluding methane, with the aid in each case of an associated function dependent on a selected physical property, preferably the molar calorific value, of the sum of the specified alkanes and in that the proportion of methane is determined from the difference between the proportion of the sum of the specified alkanes and the sum of the proportions of the alkanes determined by means of the functions.

As specified alkanes, all alkanes which are actually present in the fuel gas should, if possible, be selected and specified.

It has been found that the proportions of the alkanes in natural fuel gases are always in a particular ratio to one another which depends only on a physical property, e.g. the molar calorific value, of the sum of the specified alkanes. This is obviously attributable to the fact that natural gases in the form in which they occur have always gone through an equilibrium phase in which their gaseous and liquid phases have been in equilibrium with one another. However, the method is not restricted to natural fuel gases, either with or without addition of coal gas. For synthetic gases containing added substances or for gas mixtures having many components, the uncertainty in the determination of the gas composition is merely somewhat greater.

The molar calorific value of the sum of the specified alkanes can in turn be determined, for example, with the aid of reference signal cycles. Since the composition of the reference gases is known, their molar calorific value of the sum of the specified alkanes is also known. Consequently, from the ratio of the signals measured on the reference gases, a number corresponding to the number of reference measurement cycles of reference signal patterns can be stored with assignment to the known molar calorific values of the sum of the specified alkanes. In a future measurement cycle, the molar calorific value of the sum of the specified alkanes in the fuel gas can be determined merely by comparison of the signals measured with the stored reference signal patterns.

As functions for determining the proportions of the individual alkanes with the exception of methane, use can advantageously be made of polynomials, preferably of second order.

In a preferred illustrative embodiment, the proportions of methane, ethane, propane, isobutane, n-butane, isopentane, n-pentane, hexane, heptane and octane are determined with the aid of the functions. It has been found that the proportion of all further hydrocarbons can be ignored, particularly in the case of natural fuel gas. The relationship between the molar calorific value and the sum of the specified alkanes is in this case, e.g.:

$$X_{C2H6}=[\alpha_1(H_{CH}-H_{CH4})+\beta_1(H_{CH}-H_{CH4})^2]X_{CH} \quad (1.1)$$

$$X_{C3H8}=[\alpha_2(H_{CH}-H_{CH4})+\beta_2(H_{CH}-H_{CH4})^2]X_{CH} \quad (1.2)$$

$$X_{i-C4H10}=[\alpha_3(H_{CH}-H_{CH4})+\beta_3(H_{CH}-H_{CH4})^2]X_{CH} \quad (1.3)$$

$$X_{n-C4H10}=[\alpha_4(H_{CH}-H_{CH4})+\beta_4(H_{CH}-H_{CH4})^2]X_{CH} \quad (1.4)$$

$$X_{i-C5H12}=[\alpha_5(H_{CH}-H_{CH4})+\beta_5(H_{CH}-H_{CH4})^2]X_{CH} \quad (1.5)$$

$$X_{n-C5H12}=[\alpha_6(H_{CH}-H_{CH4})+\beta_6(H_{CH}-H_{CH4})^2]X_{CH} \quad (1.6)$$

$$X_{n-C6H14}=[\alpha_7(H_{CH}-H_{CH4})+\beta_7(H_{CH}-H_{CH4})^2]X_{CH} \quad (1.7)$$

$$X_{n-C7H16}=[\alpha_8(H_{CH}-H_{CH4})+\beta_8(H_{CH}-H_{CH4})^2]X_{CH} \quad (1.8)$$

$$X_{n-C8H18}=[\alpha_9(H_{CH}-H_{CH4})+\beta_9(H_{CH}-H_{CH4})^2]X_{CH} \quad (1.9)$$

Here, $\alpha_i$ and $\beta_i$ are constants and $H_{CH4}$ is the molar calorific value of methane. The variable $H_{CH}$ is the molar calorific value of the sum of the specified alkanes ($H_{CH}=\Sigma X_{CH,i} H_{CH,i}$). The proportion of methane is in this case determined as follows:

$$X_{CH4}=X_{CH}-(X_{C2H6}+X_{C3H8}+X_{i-C4H10}+X_{n-C4H10}+X_{i-C5H12}+X_{n-C5H12}+X_{n-C6H14}+X_{n-C7H16}+X_{n-C8H18}) \quad (2)$$

An embodiment of the invention is characterised in that the steps b) and c) are preceded by a plurality of measurement cycles in which step b) is carried out using a plurality of reference gases whose composition and whose selected physical property of the sum of the specified alkanes are known, in that the constants, e.g. coefficients, of the functions describing the proportion of the alkanes excluding methane are determined from the signals measured on the reference gases, in that the constants of the functions are stored with assignment to the respective alkanes and in that the proportion of the alkanes excluding methane is determined from a future measurement cycle on fuel gas of unknown composition with the aid of the functions.

In this way, the constants $\alpha_i$ and $\beta_i$ can be found with the aid of only two reference cycles for all natural gases. To increase the measurement accuracy, any number of reference cycles can be carried out. Even in the case of a large number of reference cycles, the effort remains comparatively low since the constants $\alpha_i$ and $\beta_i$ only have to be determined once.

The proportion of the sum of the alkanes in the fuel gas can be determined with the assumption that the fuel gas consists only of a specified number of alkanes, nitrogen and carbon dioxide. The associated equations therefore have the form:

$$X_{CH}=1-X_{N2}-X_{CO2} \quad (3)$$

Here, $X_{N2}$ and $X_{CO2}$ are the proportions of nitrogen and carbon dioxide, respectively.

To increase the measurement accuracy, it can alternatively be assumed that the fuel gas additionally contains hydrogen and/or carbon monoxide. If both the proportion of hydrogen and the proportion of carbon monoxide are taken into account, equation (3) becomes:

$$X_{CH}=1-X_{N2}-X_{CO2}-X_{H2}-X_{CO} \quad (3')$$

A preferred illustrative embodiment is characterised in that the speeds of sound under two different conditions and the calorific value can be derived from the gas composition. These parameters can be calculated in a simple way from the composition of the gas by means of an equation of state such as the AGA-8 equation frequently used for gas.

$$W_{i,calc}=f(p_i, T_i, X_{CH4}, \ldots X_{n-C8H18}, X_{CO2}, X_{N2}) \quad (4)$$

An example of an embodiment of the invention is characterised in that values for the speed of sound under first and second reference conditions and the calorific value are derived from the composition of the fuel gas, in that the difference between the derived and the measured value of the speeds of sound and the calorific value is formed, in that, if the difference exceeds a specified threshold value, the proportion of at least one of the components of the fuel gas to be determined is altered, in that the composition is recalculated on the basis of the altered value or values, the values of the selected parameters are recalculated and the difference between these and the measured values is determined and in that the latter two steps are repeated until the difference lies below the threshold value.

It has been found that the gas composition can be determined particularly quickly in this way. If all 14 equations given above (1.1 to 4) are to be taken into account, these contain up to 14 unknowns, namely $X_{CH}$, $X_{CH4}$, $X_{C2H6}$, $X_{C3H8}$, ..., $X_{n-C8H19}$, $W_{1,calc}$, $W_{2,calc}$, $H_{S,n,calc}$, $\rho_{m,n,calc}$. To solve these 14 equations, one or more values, e.g. the two speeds of sound mentioned in combination with the calorific value, can be derived and compared with the corresponding measured value.

The advantage of the method according to the invention is that not only is it possible to determine the quantity of heat supplied to consumption devices, but also other important properties of the gas such as the compressibility factor, the density, the speed of sound, the enthalpy, the methane number or the Wobbe index of the fuel gas can be calculated from the composition.

The physical parameters determined using the method of the invention are essentially as good as those determined by means of gas chromatography. According to the invention, only three measured parameters, e.g. two speeds of sound and the calorific value, are sufficient to carry out many process engineering calculations. Firstly, changes of state in gas reservoirs or storage volumes can be determined. In addition, the relevant gas transport data,.e.g. temperature or pressure drop, can be determined. For vehicles powered by natural gas, the required design of gas filling stations can be calculated.

Fill level measurements can be checked and designed using the method of the invention.

In connection with heat exchangers too, the invention is of great advantage. The design of heat exchangers can be calculated using the method of the invention. Performance measurements on heat exchangers can be evaluated using the method. Finally, compressor characteristics and compressor performances can be determined using the method of the invention.

In all the above mentioned applications, expensive gas-chromatographic analyses have previously been necessary.

The methane number, too, can be determined using the method of the invention. If the gas property data which were originally measured for charging purposes are used as input measurement signals for the method of the invention, the methane number can be calculated to essentially the same accuracy as when using a gas chromatograph. The deviation of the methane numbers is less than 2%.

When using the gas property data measured for charging purposes or when using supply network simulations, fuel gas customers can be informed at any time about current and possibly future fluctuations in the methane number without additional measurements. The gas transport network can also be controlled more flexibly without additional cost.

Further advantageous embodiments of the invention are characterised in the further and dependent claims.

The way in which the method according to the invention is used for the correlative measurement and/or regulation of the quantity of heat supplied to gas-consuming devices is explained hereafter in more detail with reference to illustrative embodiments which are illustrated in the drawing. In the drawing.

Figure 1:
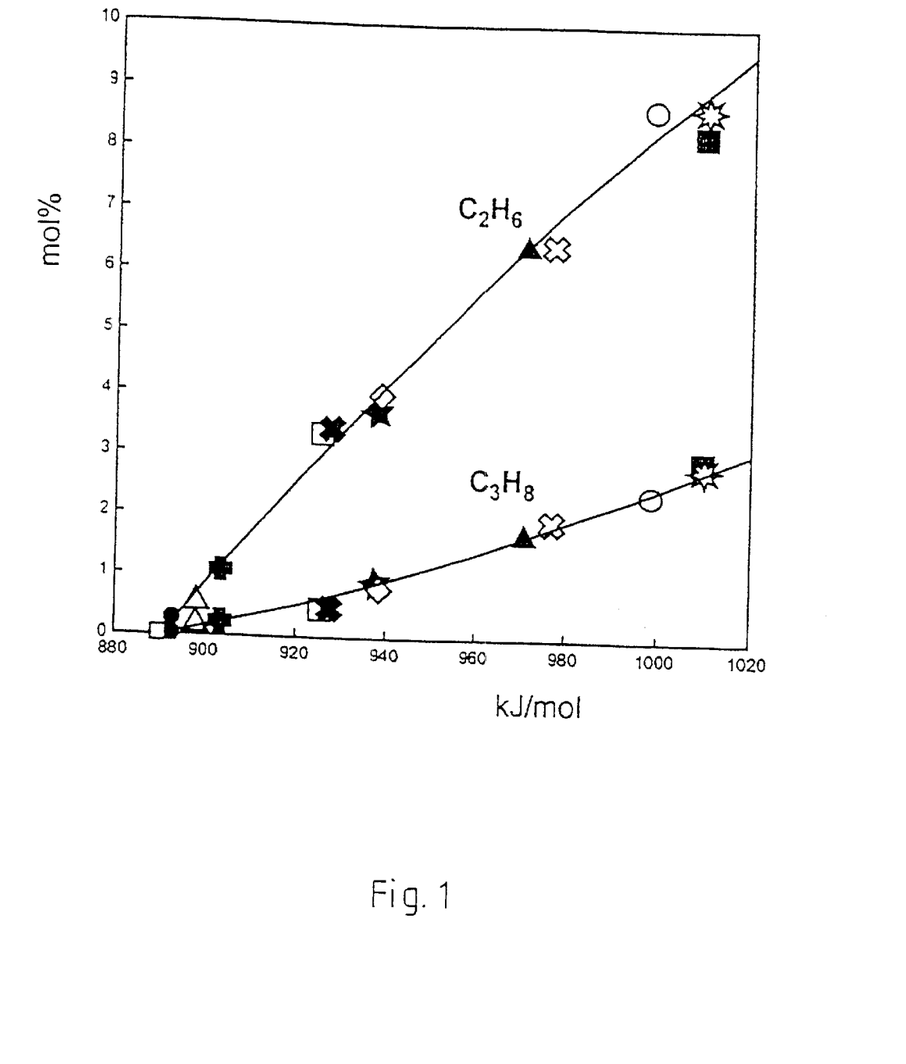
FIG. 1 shows a graph in which the mole fraction of ethane and propane for various gases is plotted against the molar calorific value of the sum of the hydrocarbons.

In FIG. 1, the molar calorific value of the sum of the alkanes ($H_{CH}$) is plotted on the x axis and the mole fraction of ethane ($C_2H_6$) and propane ($C_3H_8$) is plotted on the y axis. The corresponding values were determined for various natural gases and plotted. The proportion of both ethane and of propane was approximated by a 2nd order polynomial. As FIG. 1 shows, both the proportion of ethane and that of propane can be approximated surprisingly well by a 2nd order polynomial dependent on the molar calorific value of the sum of the alkanes. The same applies to the further alkanes up to octane. The measured values for these alkanes are, for reasons of clarity, not shown in FIG. 1.

Figure 2A:
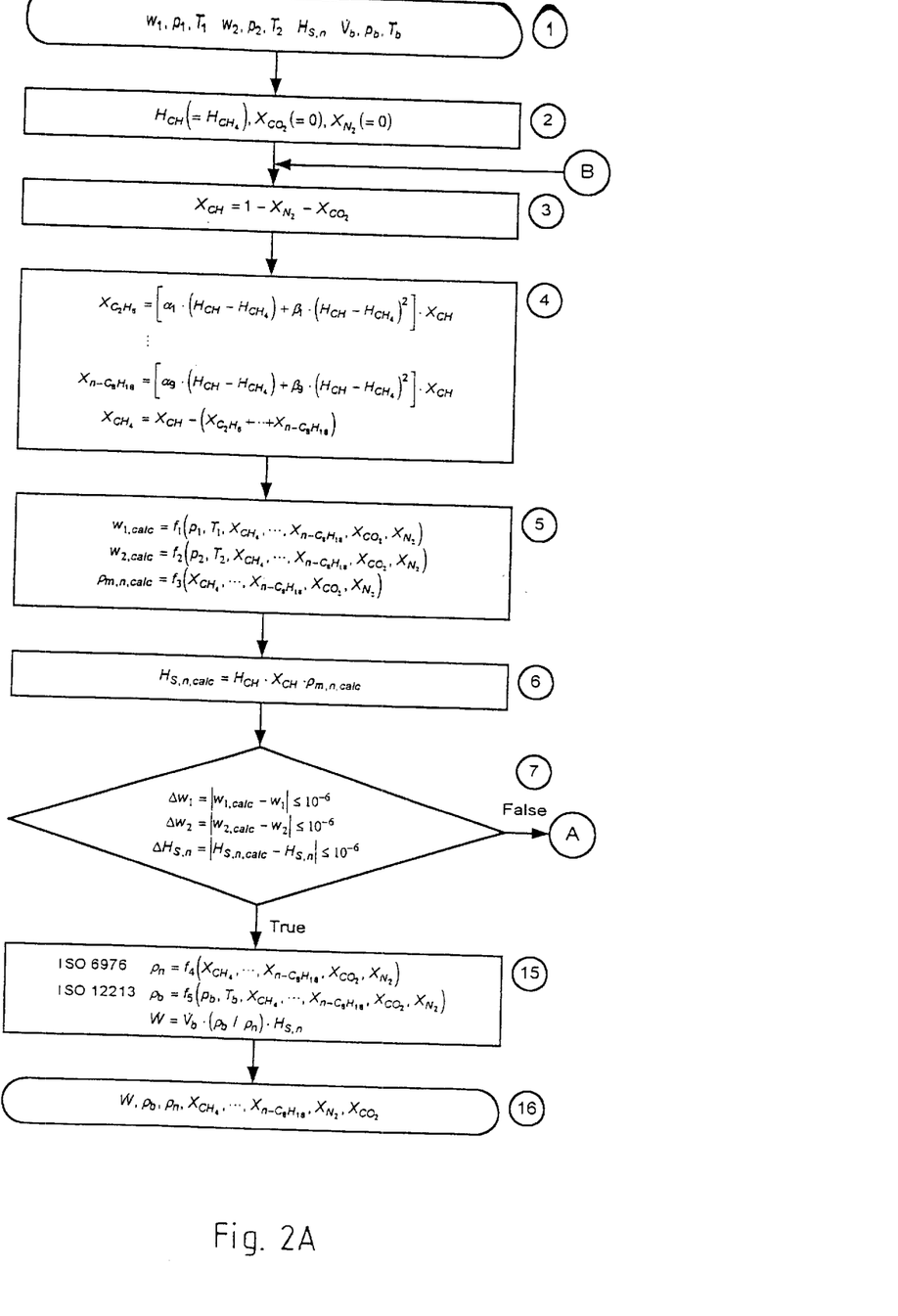
FIG. 2A and FIG. 2B show a flow diagram for the determination of the gas composition according to an illustrative embodiment of the method of the invention.
Figure 2B:
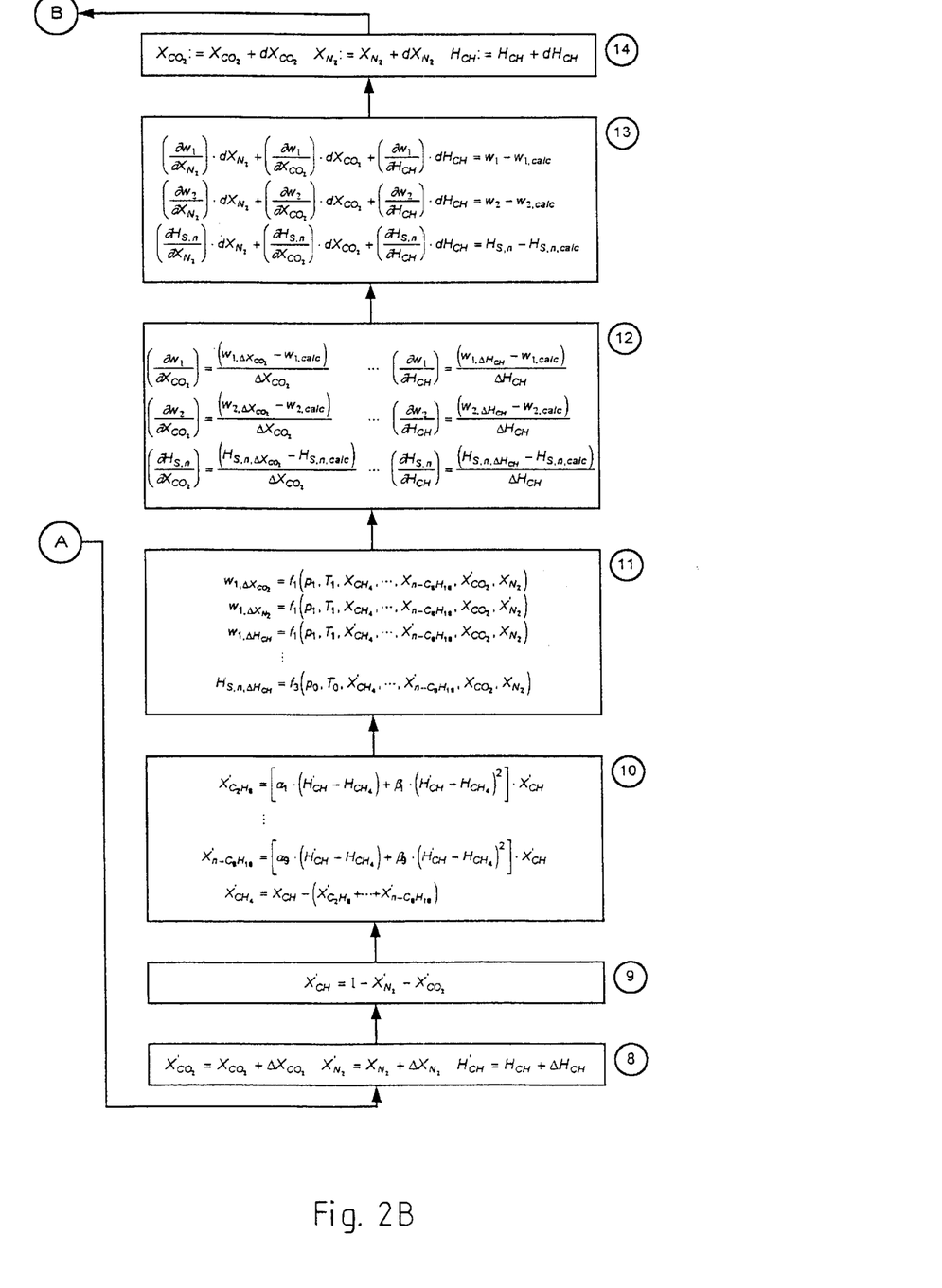

FIGS. 2A and 2B show a flow chart for determining the gas composition according to a preferred illustrative embodiment.

In step 1, two speeds of sound are measured, in each case under different conditions.

Of the conditions, the pressure is set in each case and the temperature can be set or the measurement can take place at the temperature which is established after a possible pressure change. The actual pressure and the temperature for each measurement are measured.

In Step 1, the calorific value of the fuel gas is also made available. If the calorific value of the fuel gas exhibits relatively few fluctuations, it may be advantageous to use a fixed value. The calorific value of the fuel gas may also be made available by a measuring appliance.

In step 2, starting values for the molar calorific value of the sum of the alkanes ($H_{CH}$), the proportion of nitrogen $X_{N2}$ and the proportion of carbon dioxide $X_{CO2}$ are determined. For the starting values, it is also possible to use the data for pure methane, i.e. $X_{CO2}=0$, $X_{N2}=0$ and $H_{CH}=H_{CH4}$. In practice, good results are achieved using these starting values.

Using the starting values for the proportion of nitrogen and the proportion of carbon dioxide, the proportion of the sum of the alkanes $X_{CH}$ is then determined in step 3.

In step 4, the proportion of the alkanes excluding methane is then determined with the aid of the molar calorific value of the sum of the alkanes $H_{CH}$ and the equations (1.1) to (1.9). Subsequently, the proportion of methane $X_{CH4}$ is determined using equation (2). With the aid of an equation of state, values for the speed of sound under the same conditions as for the values measured in step 1 are then calculated in step 5 from the calculated composition of the gas. This can be done, for example, with the aid of the known AGA8-DC92 equation of state.

In Step 5, the molar density $\rho_{m,n,calc}$ in mol/m$^3$ of the fuel gas under normal conditions is also calculated from the calculated composition of the gas. A suitable calculation method for determining the molar density of the fuel gas under normal conditions is described, for example, in ISO 6976.

In Step 6, the calorific value of the fuel gas is calculated from the calculated composition of the fuel gas.

In step 7, a check is made as to whether the absolute value of the difference between the calculated values of the speed of sound $W_{1,calc}$, $W_{2,calc}$, $H_{S,n,calc}$ and the values $w_1$, $w_2$, $H_{S,n}$ measured in step 1 is, for each value, less than the threshold value which has been laid down as $10^{-6}$. If not, the procedure is continued from step 8.

In steps 8 to 12, the sensitivity of the parameters $X_{N2}$, $X_{CO2}$ and $H_{CH}$ used in the iteration process is determined. For this purpose, values for $\Delta X_{N2}$, $\Delta X_{CO2}$ and $\Delta H_{CH}$ are first laid down in step 8. Good results are achieved using 0.1 mol % for $\Delta X_{N2}$ and $\Delta X_{CO2}$ and 1.0 MJ/mol for $\Delta H_{CH}$.

In step 9, the sum of the alkanes $X'_{CH}$ is calculated from the new values of the proportion of carbon dioxide $X'_{CO2}$ and the proportion of nitrogen $X'_{N2}$ using equation (3).

Subsequently, in step 10, the proportion of alkanes excluding methane is determined using the new molar calorific value of the sum of the alkanes $H'_{CH}$ and the equations (1.1) to (1.9) and, finally, the proportion of methane $X'_{CH4}$ is calculated by means of equation (2).

In step 11, the values of the speed of sound are determined under the two different conditions employed in step 1. Also the calorific value of the fuel gas at normal conditions is calculated. Here, only one of the three input parameters is varied in each case. After completion of step 11, values for the speed of sound and the calorific value as a function of $X'_{CO2}$, $X'_{N2}$ and $H'_{CH}$ have thus been obtained for each condition.

Subsequently, the partial derivatives are determined in step 12. For this purpose, the change in both speeds of sound and the calorific value as a function of one of the input parameters is first determined. For this purpose, the difference between the values of the speed of sound and the calorific value calculated in step 11, with one of the input parameters being changed slightly, and the values calculated in step 5 and 6 are determined. The partial derivative can now be calculated in a simple way from the quotient of the above mentioned change in the speed of sound or the calorific value and the change in the input parameter concerned laid down in step 8.

In Step 13, the generally applicable equations are solved in order to describe the development of variations in the input parameters in an output variable. After the values of the partial derivatives have been substituted, the system of linear equations can easily be solved by means of generally known mathematical techniques. The result is estimates of the deviations of parameters $X_{N2}$, $X_{CO2}$ and $X_{CH}$.

In step 14, the new values for the proportion of nitrogen $X_{N2}$, the proportion of carbon dioxide $X_{CO2}$ and the molar calorific value of the sum of the specified alkanes $H_{CH}$ are laid down afresh by simply adding the deviations in these three parameters calculated in step 11 to the previous values.

Steps 3 to 7 are then repeated using the freshly laid down value for the proportion of nitrogen $X_{N2}$, the proportion of carbon dioxide $X_{CO2}$ and the molar calorific value of the sum of the specified alkanes $H_{CH}$. If, in step 7, the threshold values of $\Delta w_1$, $\Delta w_2$ and/or $\Delta H_{S,n}$ are again exceeded, steps 8 to 14 and 3 to 7 are carried out once again. Only when $\Delta w_1$, $\Delta w_2$ and $\Delta H_{S,n}$ are below the threshold value of $10^{-6}$ in step 7, the proportions of the alkanes, the proportion of carbon dioxide and the proportion of nitrogen are established to the desired degree of accuracy.

In this latter case, all desired gas parameters are then calculated in steps 15 and 16. This is done with the aid of the known ISO 6976 and ISO 12213.

The quantity of heat supplied can now be calculated without difficulty, for example by firstly calculating the volumetric flow rate under normal conditions, with the aid of the calculated values for the density under operating conditions and the density under normal conditions, and using the measured volumetric flow rate under operating conditions. Multiplication of the volumetric flow rate under normal conditions and the calorific value under normal conditions gives the quantity of heat supplied.

The method described can be carried out in a similar way for the other combinations of parameters mentioned above.

The value calculated is suitable for the measurement and/or regulation of the quantity of heat supplied to gas-consuming devices, in particular to natural-gas-consuming devices.

For the purposes of the present invention, gas consumption devices are all necessary devices for the use of gas on the premises of private and industrial customers and also all transfer points or the like.

According to the invention, the quantity of heat supplied to households can already be derived from four parameters, i.e., firstly, the volume or the mass, secondly, two speeds of sound, and thirdly, the calorific value. The technical difficulty and the costs of such derivation are minimal.

To increase the accuracy, it is possible, as in the measurement of the calorific value, to determine as many further parameters as desired. For applications in which particularly high measurement accuracy is required, e.g. for determining the amount of heat supplied at transfer points of main transport lines having a high gas throughput, it is advantageous to measure the pressure and the temperature in addition to the above three parameters. When a lower measurement accuracy is permissible, estimated values can also be used for these parameters.

Figure 3:
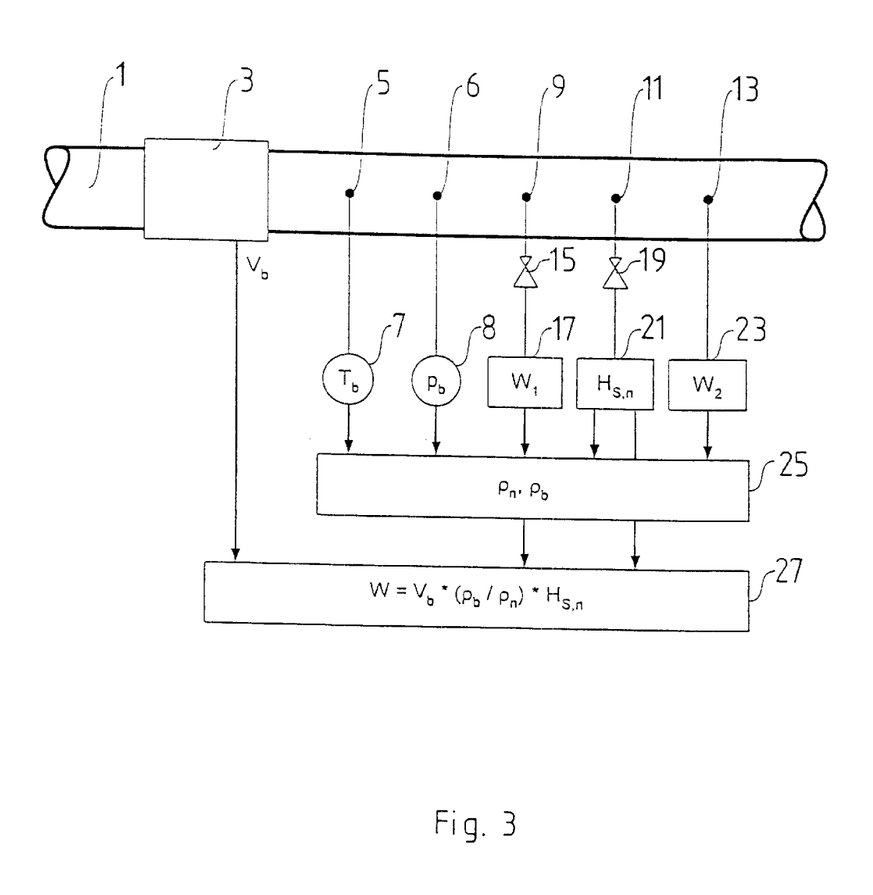
FIG. 3 shows a schematic view of an arrangement for carrying out a first illustrative embodiment of the use according to the invention of the method of measuring the quantity of heat.

FIG. 3 shows a fuel gas line 1 in which a gas meter 3 is located. In addition, two measurement points 5 and 6 are located in the fuel gas line 1. Measurement point 5 is provided with a temperature sensor 7 and measurement point 6 is provided with a pressure sensor 8. Furthermore, three sample points 9, 11 and 13 are provided in the fuel gas line. Sample point 9 is connected via a pressure-reducing valve 15 to a measuring apparatus for measuring the speed of sound under first reference conditions 17. Sample point 11 is connected via a pressure-reducing valve 19 to a measuring apparatus for measuring the calorific value at normal conditions 21. Sample point 13 is connected to a measuring apparatus for measuring the speed of sound under operating conditions 23.

In the operating state, the gas meter 3 measures the volume flow $V_b$ and the time and, from this, calculates the volume of the fuel gas supplied. The temperature sensor 7 measures the temperature and the pressure sensor 8 measures the pressure in the fuel gas line 1.

The signal outputs from the temperature sensor 7, the pressure sensor 8 and the measuring devices 17, 21 and 23 are connected to the inputs of a correlation calculator 25, for the correlative determination of the density under operating conditions $\rho_b$ and of the density under normal conditions $\rho_n$, either direct from the measurement variables recorded or using the iterative method described above.

The output of this correlation calculator and the signal output of the gas meter 3 and the output of the device for measuring the calorific value at normal conditions are connected to the inputs of the energy calculator 27.

Then, the energy calculator 27 calculates the quantity of heat W by multiplying $H_{SV,n}$ of the volume under operating conditions $V_b$, the density under operating conditions $\rho_b$, the density under normal conditions $\rho_n$ and the calorific value under normal conditions. In the practical configuration, the correlation calculator and the energy calculator are integrated as successive programme steps in a computer.

Figure 4:
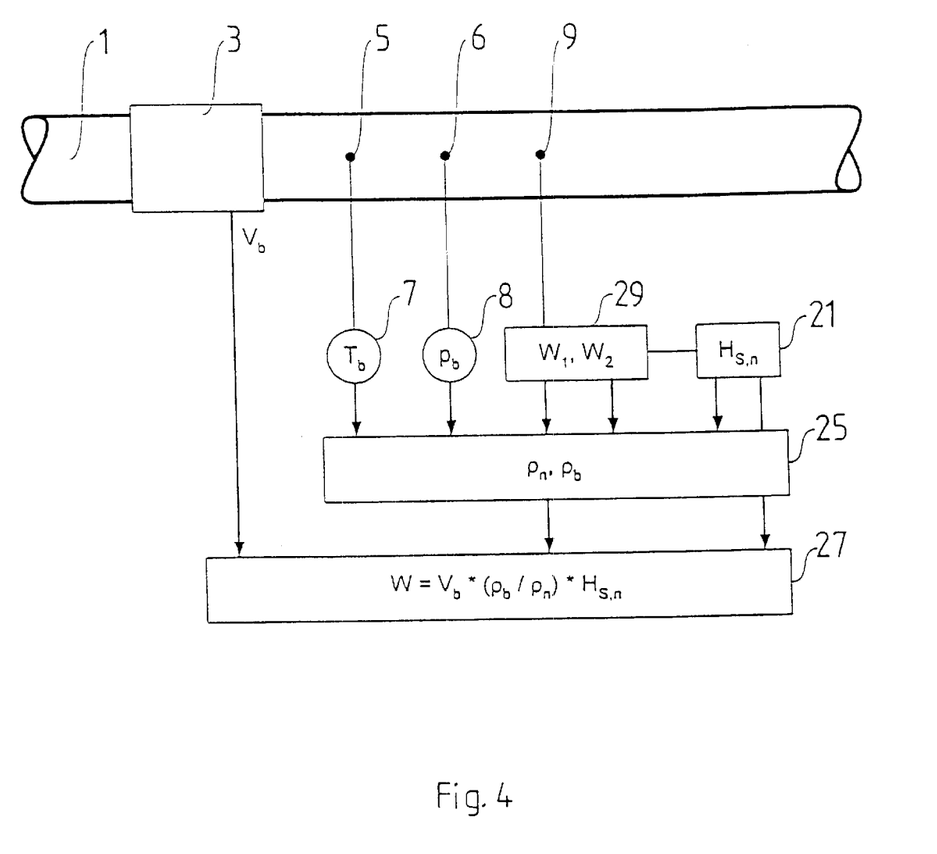
FIG. 4 shows a schematic view of an arrangement for carrying out a second illustrative embodiment of the use according to the invention.

FIG. 4 shows an arrangement for carrying out a second illustrative embodiment of the invention. The arrangement in FIG. 4 differs from the arrangement in FIG. 3 in that both speeds of sound are measured in a measuring apparatus 29 for measuring the speed of sound. The fuel gas is fed directly without a pressure reduction to the measuring apparatus 29 so that the speed of sound can be measured directly under operating conditions. Measuring apparatus 29 is provided with a means for increasing or lowering the pressure to the range of the first or second reference conditions. The measuring apparatus 29 is connected via a gas line to a measuring apparatus 21 for determining the calorific value.

In this illustrative embodiment, the amount of heat is calculated by the energy calculator 27 via the correlation calculator 25, as in the first illustrative embodiment, on the basis of the volume, the temperature and the pressure under operating conditions, the speed of sound under first reference conditions, the speed of sound under operating conditions and the calorific value at normal conditions. Since in both the illustrative embodiments shown in FIG. 3 and FIG. 4 the measuring apparatus for the speed of sound and the calorific value are located outside the fuel gas line, maintenance of these apparatus and any repair can be carried out without any particular technical difficulty. In addition, only comparatively few reference cycles are required, since the speeds of sound are measured under specified conditions. There is thus a direct correlation between a change in the speeds of sound and a change in the gas composition.

Figure 5:
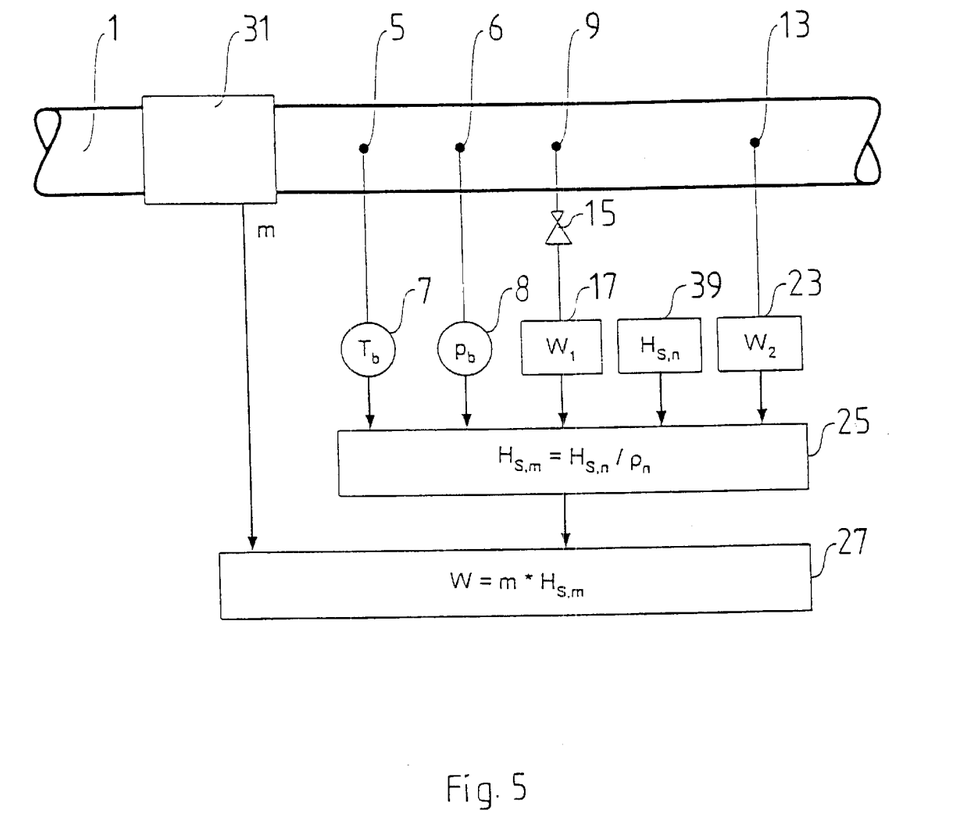
FIG. 5 shows a schematic view of an arrangement for carrying out a third illustrative embodiment of the use according to the invention.

FIG. 5 schematically shows a third illustrative embodiment of the invention. The arrangement differs from the arrangement shown in FIG. 4 in that a mass flow meter 31 for measuring the mass of the fuel gas supplied is provided in place of the volume meter Furthermore, the calorific value is not measured, but rather is input directly into the correlation calculator 25 as a fixed value 39.

The correlation calculator 25 firstly calculates the density under normal conditions $\rho_n$ by correlation. Then, the correlation calculator calculates the mass-related calorific value $H_{S,m}$ from the division of the calorific value under normal conditions $H_{S,n}$ and the density under normal conditions $\rho_n$. Then, the energy calculator 27 calculates the quantity of heat W by multiplying the calorific value $H_{s,m}$ by the mass M.

Figure 6:
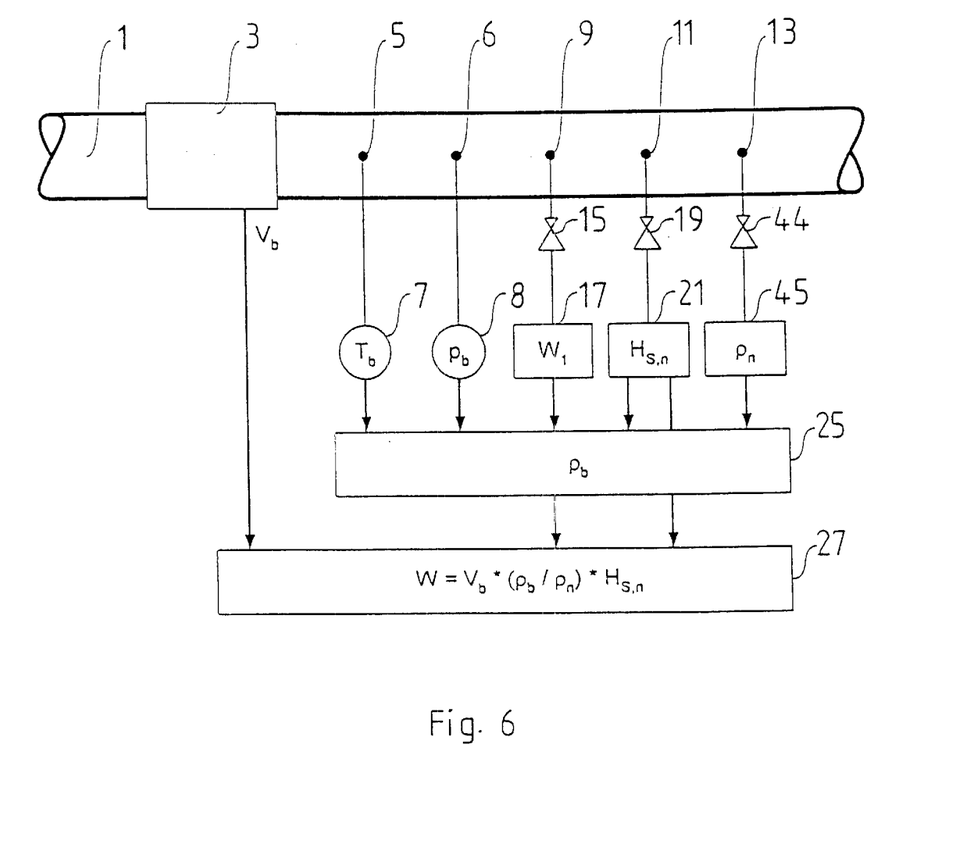
FIG. 6 shows a schematic view of an arrangement for carrying out a fourth illustrative embodiment of the use according to the invention.

FIG. 6 schematically depicts a fourth illustrative embodiment of the invention. The arrangement differs from the arrangement in accordance with FIG. 3 in that the density under normal conditions is determined instead of the speed of sound under operating conditions. To do this, the sample point 13 is connected to a measuring device for determining the normal density 45 via a pressure-reducing valve 44.

Firstly, the correlation calculator 25 calculates the density under operating conditions by correlation. Then, the energy calculator 27 calculates the quantity of heat W by multiplying the calorific value $H_{SV,n}$ of the volume under operating conditions $V_b$, the density under operating conditions $\rho_b$, the density under normal conditions $\rho_n$ and the calorific value under normal conditions.

Figure 7:
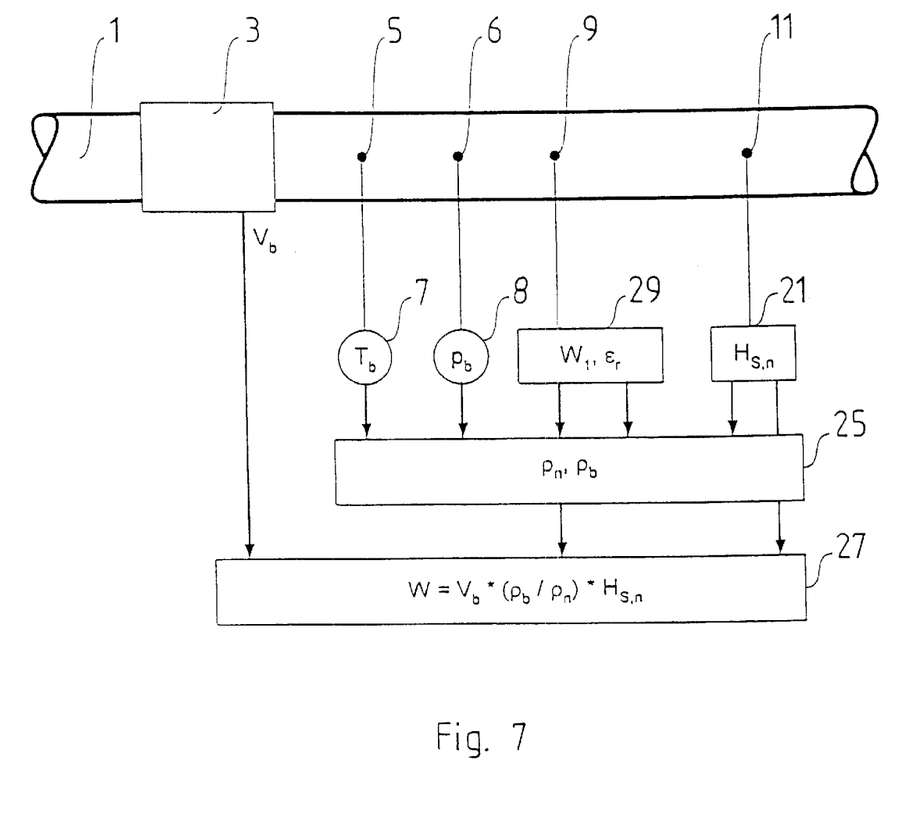
FIG. 7 shows a schematic view of an arrangement for carrying out a fifth illustrative embodiment of the use according to the invention.

FIG. 7 schematically depicts a fifth illustrative embodiment of the invention. The arrangement differs from the arrangement in accordance with FIG. 4 in that instead of the two speeds of sound, the dielectric constant and the speed of sound under first reference conditions are determined in a measuring device. For this purpose, the sample point 9 is directly connected to the measuring device 29. Moreover, in this case, in contrast to the second example, the measuring device 21 for determining the calorific value is directly connected to the fuel-gas line 1 by means of a separate sample point 11.

All illustrative embodiments have the advantage that it is not necessary to carry out measurements of the speed of sound in order to determine the amount of heat reliably, because the necessary data can be derived from the known relationships between the gas composition and the speed of sound. These known data can be utilised to derive the calorific value from the speed of sound.

It is also possible to arrange some of the devices for determining the measurement variables under operating conditions inside the fuel-gas line. Naturally, in this specific case, only non-combustive methods are suitable for determining the calorific value.

Furthermore, the joint measurement environment for the dielectric measurement and the measurement of the proportion of carbon dioxide and the measurements of the speed of sound has the advantage that only one pressure and temperature measurement is required in addition to the pressure and temperature measurement in the fuel gas line. The third illustrative embodiment has a particularly high accuracy in the determination of the amount of heat and is therefore particularly advantageous. It is also possible to locate some of the apparatus for determining the parameters under operating conditions inside the fuel gas line.

What is claimed is:

1. A direct method for measuring and/or regulating a quantity of heat contained in a fuel gas, using the calorific value of the fuel gas as an input parameter, wherein said calorific value is measured value, inputted once, or a value measured and inputted at regular intervals or continuously, comprising a) guiding the fuel gas or a part-stream of the fuel gas through a volumetric meter or a mass flow meter, and measuring the volumetric flow rate or the mass flow rate, b) determining the speed of sound of the gas under first reference conditions, c) recording one of the measurement variables selected from dielectric constant, speed of sound under second reference conditions, carbon dioxide content of the fuel gas, nitrogen content of the fuel gas and density under standardized conditions, d) calculating required densities values or a density correlated calorific value, and e) deriving the quantity of heat supplied from the parameters obtained in b)–d) and from the measured value for the calorific value of the fuel gas, as a measurement variable or control variable.

2. Method according to claim 1, wherein a pressure between 1 and 10 bar and a temperature above 225 K are set as the first reference conditions for measuring the speed of sound.

3. Method according to claim 1, wherein a pressure of over 30 bar and a temperature of between 225 K and 350 K are set as the second reference conditions for measuring the speed of sound.

4. Method according to claim 1, wherein operating conditions are set as the second reference conditions.

5. Method according to claim 1, wherein in step a), in addition, at least one of the measurement variables temperature or pressure is recorded.

6. Method according to claim 1, wherein a plurality of measurement cycles are connected upstream of the method steps a) and b), in which measurement cycles the step a) is carried out using a plurality of reference gases of known calorific value; in that from the ratio of the various measurement signals recorded for the reference gases, a number of reference signal samples which corresponds to the number of measurement cycles is stored by being assigned to the known calorific values; and in that the signal sample from a later measurement cycle carried out on fuel gas of unknown calorific value is compared with the reference signal samples in order to assign a defined calorific value.

* * * * *